(12) United States Patent
Foss et al.

(10) Patent No.: US 7,201,068 B2
(45) Date of Patent: Apr. 10, 2007

(54) WATER CUT METER FOR MEASUREMENT OF WATER IN CRUDE OIL

(75) Inventors: Gary C. Foss, Renton, WA (US); Matthew R. Tavares, Federal Way, WA (US); Richard R. Basham, Kent, WA (US)

(73) Assignee: The Boeing Company, Chicago, IL (US)

( * ) Notice: Subject to any disclaimer, the term of this patent is extended or adjusted under 35 U.S.C. 154(b) by 840 days.

(21) Appl. No.: 10/611,397

(22) Filed: Jun. 30, 2003

(65) Prior Publication Data

US 2006/0212232 A1    Sep. 21, 2006

(51) Int. Cl.
*G01F 1/28* (2006.01)
(52) U.S. Cl. .................................. 73/861.74
(58) Field of Classification Search ............. 73/304 C, 73/861.04, 61.44, 195, 861.74
See application file for complete search history.

(56) References Cited

U.S. PATENT DOCUMENTS

| 5,095,758 A | 3/1992 | Cox et al. |
| 5,127,272 A | 7/1992 | Dean et al. |
| 5,249,455 A | 10/1993 | Cox |
| 5,259,239 A | 11/1993 | Gaisford |
| 5,272,444 A | 12/1993 | Cox |
| 6,076,049 A | 6/2000 | Lievois et al. |
| 6,234,030 B1 | 5/2001 | Butler |
| 6,292,756 B1 | 9/2001 | Lievois et al. |
| 6,318,156 B1 | 11/2001 | Dutton et al. |
| 6,318,172 B1 | 11/2001 | Byatt et al. |

*Primary Examiner*—Jewel Thompson
(74) *Attorney, Agent, or Firm*—Lee & Hayes, PLLC (57) ABSTRACT

An apparatus, systems, and methods for measuring an amount of oil in a flow of fluid are provided. A housing defines an interior passage configured to pass a flow of fluid. A capacitance sensor, which suitably is a pair of insulated electrodes, is configured to respond to a capacitance of the flow of fluid is disposed within the interior passage of the housing. The capacitance sensor is coupled to conductors through which a first analog signal is generated. These conductors can be engaged to measure the capacitance of the flow of fluid. A conductance sensor configured to measure conductance of the flow of fluid also is disposed on the interior passage of the housing and generates a conductance signal as a second analog signal. The first and second analog signals can be used to assess the relative percentages of oil and water in the flow of fluid.

84 Claims, 4 Drawing Sheets

WATER CUT METER FOR MEASUREMENT OF WATER IN CRUDE OIL

FIELD OF THE INVENTION

This invention relates generally to oil drilling and, more specifically, to measuring an amount of oil produced by a well.

BACKGROUND OF THE INVENTION

Production of oil and related petrochemicals generally begins with drilling wells into the Earth's crust to tap underground oil reserves. Drilling oil wells represents a considerable investment because the wells often must be drilled in remote locations and/or be drilled very deeply to reach oil. Moreover, the investment is a risky proposition because the drilling may not reach oil.

Considering how expensive and risky it is to drill oil wells, maintaining the wells is an important concern. If a well stops being productive, it is desirable to shut down the well rather than wastefully invest in its continued operation. Thus, it is desirable to monitor a well's production to determine whether it continues to be a viable well. Even more importantly, it is desirable to monitor a well's production to prevent a productive well from being lost. On occasion, a well's production may decline sharply if the well should become blocked or otherwise impeded. If timely action is taken to address the impediment, the well can continue to be productive. On the other hand, without timely action, the well can be lost permanently, resulting in a waste of the investment to drill and maintain the well to that point.

Monitoring a well's production to review its viability or prevent loss of the well is not a simple proposition. The output of such wells usually includes not only oil, but, also natural gas, water, and other substances. It is not desirable to invest in continued operation of an oil well that is yielding only water. More importantly, a formerly oil-producing well beginning to increasingly yield water may indicate a serious problem. If the problem is left untreated, the well could be lost.

A flow meter alone may indicate that the well is producing when, in fact, the well is producing only water. As a result, a more precise form of monitoring is desired. Unfortunately, valuable oil can exist in many different consistencies ranging from a prototypical thick, black crude to a very thin, gasoline-like fluid. Thus, successfully augmenting the flow meter to determine production of oil is not as simple as gauging the thickness of a flow of fluid being produced. An accurate assessment of the percentage of the water contained in the flow of fluid, known as a "water cut," is desired to be able to actually assess the well's production.

To address this need, a number of different technologies have been devised to measure oil production. Unfortunately, these technologies tend to involve devices that are expensive, large, delicate, and highly sophisticated. For example, oil measuring devices using gamma rays or microwaves can monitor a flow of fluid drawn from a well and accurately gauge the amount of oil contained in that flow. Unfortunately, these devices also present a number of drawbacks, foremost of which is that these devices tend to be very expensive. As a result, it is not practical to acquire such a device for each well to continually monitor the well's production. Typically, these devices are moved around to periodically spot-check various wells. Moving these devices around in itself is a problem because the equipment is large and heavy, and must be carried by truck from site to site. Unfortunately, by the time a well is due for spot-check and the equipment is moved on-site, a permanent problem may have arisen resulting in the well already having been lost.

Current technologies also present other concerns. Devices using radiation, to name one example, can be sensitive and require sophisticated care for routine upkeep. Moreover, radiation devices beyond a certain nominal output need to be licensed and regulated, adding to the complexity of their use. Moreover, such devices, used improperly, can present an environmental or human hazard.

To improve on these technologies, researchers have focused on ways to separate oil from foreign matter, natural gas, water, and other substances in the well. If the oil can be separated, then it can be a relatively simple matter to gauge a quantity of oil being produced. Given time, this separation is not a problem. Foreign matter can be separated from the oil by passing it through a filtering medium, comparable with the way that foreign matter is filtered from an automobile's oil supply by passing the automobile's oil through an oil filter. Separating the natural gas also is usually not difficult, because the less dense natural gas expands and rises out of the oil. In addition, given time, mixed oil and water also will separate themselves. Oil has a lesser density than water. Thus, if mixed oil and water are left in a collection tank, the oil will rise to the top and the water will sink to the bottom. The oil can then be collected by siphoning the oil off the top of the tank, or the water can be drained from the bottom of the tank, leaving only the oil in the tank. However, it may not be practical to allow enough time for mixed oil and water to separate themselves. Further, faster technologies to separate oil from other fluids and substances continue to prove to be complicated, difficult, and/or costly.

Thus, there is unmet need in the art for a better, cheaper, and safer way to measure an amount of oil contained in a flow of fluid extracted from an oil well.

SUMMARY OF THE INVENTION

The present invention provides an apparatus, system, and method for inexpensive and reliable measurement of an amount of oil within a flow of fluid extracted from a well. In general, capacitance of a fluid represents a good measure of a relative amount of oil contained in the flow of fluid when the flow of fluid contains approximately not more than one-half water, although capacitance does not provide as clear a measure for fluids that are more than one-half water. On the other hand, conductance of a fluid generally represents a good measure of a relative amount of oil contained in the flow of fluid when the flow of fluid contains approximately not less than one-half water, although conductance does not provide as clear a measure for fluids that are less than one-half water. Thus, combining measurement of capacitance and conductance provides a good measure of the relative amount of oil and water in a flow of fluid regardless of the relative percentage of each contained in the flow of fluid.

More particularly, embodiments of the present invention provide an apparatus, system, and method for measuring an amount of oil in a flow of fluid. A housing defines an interior passage configured to pass a flow of fluid. A capacitance sensor configured to respond to a capacitance of the flow of fluid is disposed within the interior passage of the housing. The capacitance sensor is coupled to conductors through which a first analog signal is generated. These conductors can be engaged to measure the capacitance of the flow of fluid. A conductance sensor configured to measure conductance of the flow of fluid also is disposed on the interior passage of the housing and generates a conductance signal as a second analog signal. The first and second analog signals can be used to assess the relative proportions of oil and water in the flow of fluid.

In accordance with an aspect of the present invention, a control module is operably coupled to the conductors and the conductance signal. The control module is configured to measure a capacitance of the flow of fluid. The first analog signal representative of the capacitance of the flow of fluid and the second analog signal representative of the conductance of the flow of fluid are generated by the control module.

In accordance with still further aspects of the invention, the first and second analog signals can be digitized and provided to a computing module configured to calculate the proportion of oil in the flow of fluid based on the first and second digital signals. A flow rate sensor can be included and its output combined with the proportion of oil in the flow of fluid to arrive a total rate of flow of oil. Other sensors can be added to measure pressure, density, and temperature of the flow of fluid and the total rate of flow of oil can be adjusted to reflect these parameters. Data collected and generated can be communicated to a data collection device for monitoring.

BRIEF DESCRIPTION OF THE DRAWINGS

The preferred and alternative embodiments of the present invention are described in detail below with reference to the following drawings.

DETAILED DESCRIPTION OF THE INVENTION

By way of overview, embodiments of the present invention provide an apparatus, system, and method for measuring an amount of oil in a flow of fluid. A housing defines an interior passage configured to pass a flow of fluid. A capacitance sensor configured to respond to a capacitance of the flow of fluid is disposed within the interior passage of the housing. The capacitance sensor is coupled to conductors through which a first analog signal is generated. These conductors can be engaged to measure the capacitance of the flow of fluid. A conductance sensor configured to measure conductance of the flow of fluid also is disposed on the interior passage of the housing and generates a conductance signal as a second analog signal. The first and second analog signals can be used to assess the relative percentages of oil and water in the flow of fluid.

Figure 1:
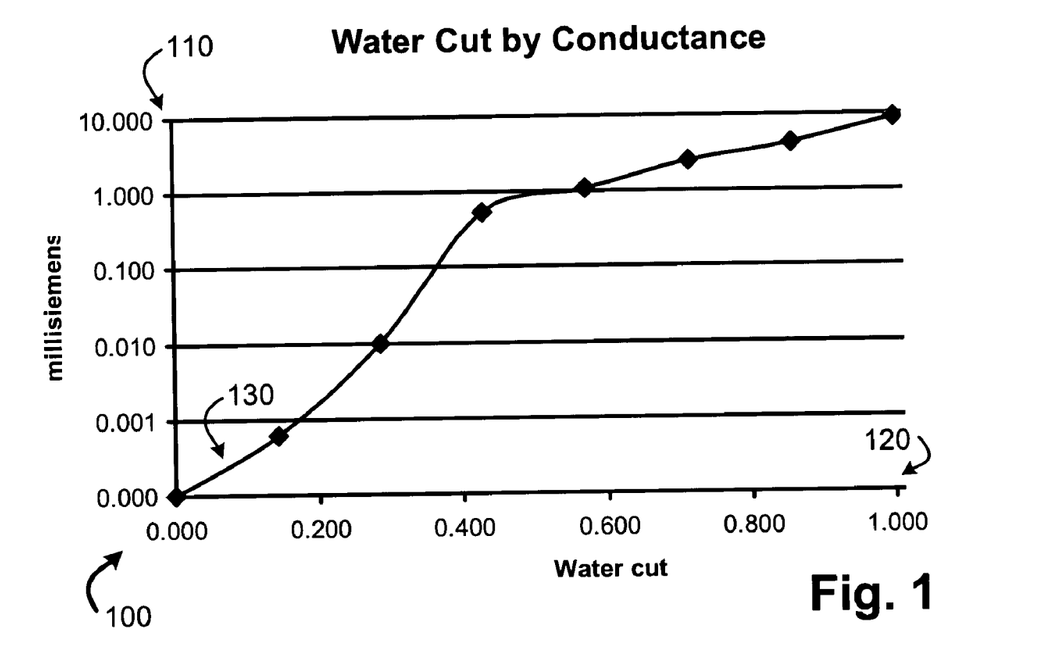
FIG. 1 is a graph of conductance versus a fractional amount of water in a flow of fluid including oil and water.

Referring to FIG. 1, a graph 100 plots conductance versus a fractional amount of water, or "water cut," in a flow of fluid including oil and water. The water component of the flow of fluid drawn from an oil well has a salinity level comparable to sea water and, thus, is conductive. By contrast, oil is not conductive. Thus, the relative proportion of oil to water in the flow of fluid can be determined by measuring the conductance of the flow of fluid. The graph 100 plots on a logarithmically-scaled vertical axis 110 conductance of a flow of fluid measured in millisiemens for a fractional amount of water plotted on the horizontal axis 120. The fractional amount of water plotted ranges from no water to all water. As can be seen from the graph 100, a curve 130 plotting the conductance has a fairly linear slope in the range of one-half water to approximately all water. On the other hand, for fluids having less than one-half water, the fluid may not conduct consistently or may not conduct at all. As the fluid becomes not at all conductive where there is almost no water or no water in the flow of fluid, resistance of the flow of fluid rises sharply, and conductance becomes a poor standard by which to measure the relative amounts of oil and water in the flow of fluid. Put another way, in a flow of fluid including oil and water, conductance accurately differentiates an amount of oil in a flow of fluid containing approximately less than one-half oil.

Figure 2:
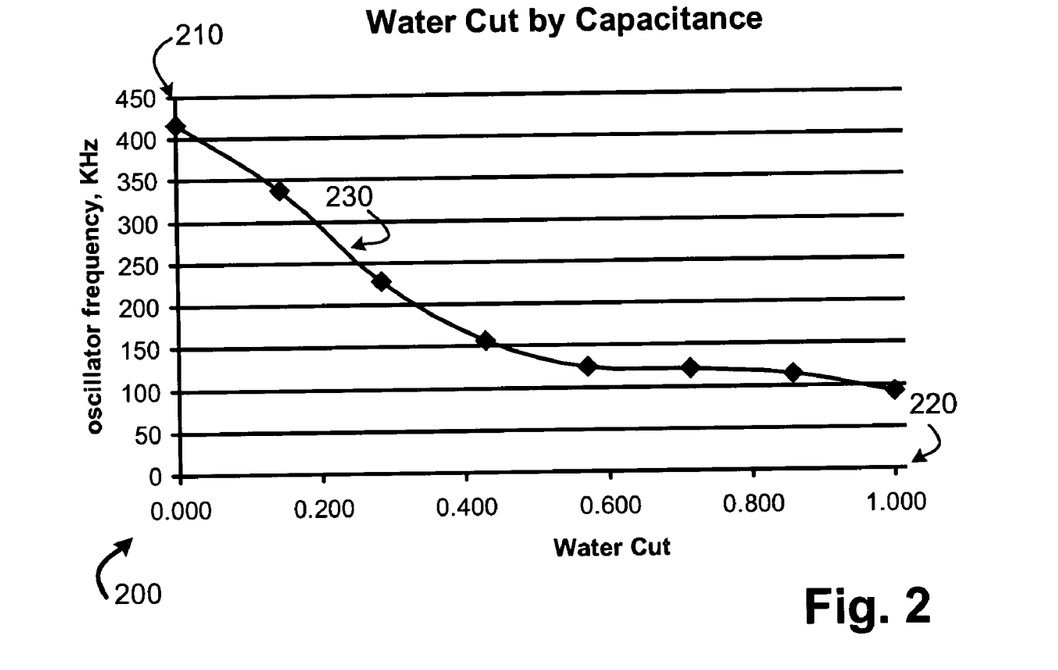
FIG. 2 is a graph of capacitance versus a fractional amount of water in a flow of fluid including oil and water.

Referring now to FIG. 2, a graph 200 plots capacitance versus a fractional amount of water in a flow of fluid including oil and water. Oil is a known dielectric while water is not dielectric. Attempting to measure the capacitance of the flow of fluid effectively makes the flow of fluid the capacitor in a RC oscillator circuit which yields a self-excited oscillation. A changing capacitance value changes the frequency of that oscillation. Because the relative amount of oil in the flow of fluid changes the capacitance of the fluid, the relative amount of oil in the flow of fluid changes the oscillation measured. The oscillation frequency representing capacitance of the fluid is plotted against a fractional amount of water plotted on the horizontal axis 220. As in the graph 100 (FIG. 1), the fractional amount of water plotted ranges from no water to all water. As can be seen from the graph 200, a curve 230 plotting the capacitance has a fairly linear slope in a range between approximately no water and one-half water, but the slope flattens out with further increasing amounts of water. As the relative amount of water in the flow of fluid increases, the flow of fluid tends to become more of a conductor, and its capacitance becomes less of a useful measure of the amount of oil in the flow of fluid. Thus, capacitance differentiates fractional amounts of water for flows of fluid containing no more than approximately one-half water. Viewed another way, in a flow of fluid including oil and water, capacitance differentiates an amount of oil in the flow of fluid including up to approximately one-half oil.

Because the conductance and capacitance provide useful, complementary measures of the relative percentages of water and oil in a flow of fluid including both, according to the present invention, measuring both conductance and capacitance advantageously provides a useful way to measure the relative percentages of water and oil in the flow of fluid. When the measurements of one or both of conductance or capacitance indicate that the flow of fluid is less than approximately one-half oil, conductance is selected as the principal measure of the relative percentage of oil in the flow of fluid. On the other hand, when the measurements of one or both of conductance or capacitance indicates that the flow of fluid is not less than approximately one-half oil, capacitance is selected as the principal measure of the relative amount of oil in the flow of fluid. Measuring both quantities and selecting the more applicable measure for the composition of the flow of fluid advantageously allows for an accurate measurement regardless of the proportions of oil and water in the flow of fluid.

Figure 3:
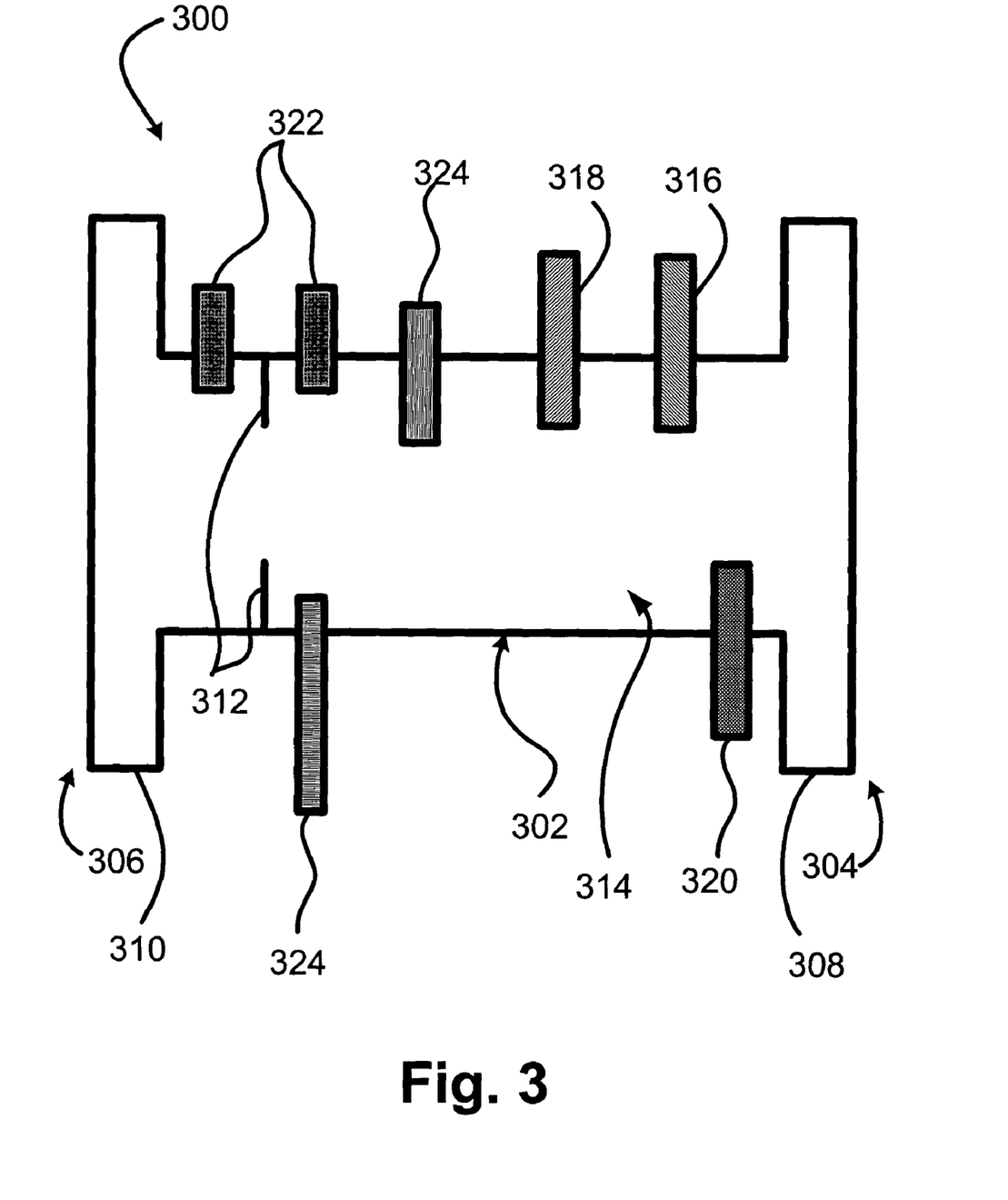
FIG. 3 is a cross-sectional diagram of a measuring device according to an embodiment of the present invention.

FIG. 3 is a cross-sectional diagram of a measuring device 300 according to an embodiment of the present invention.

One presently preferred embodiment of the device includes a housing 302 including a section of flanged pipe. A first input end 304 is coupled with a source of a flow of fluid (not shown) and a second outlet end 306 is coupled with an outlet for the flow of fluid. Flanges 308 and 310 and the first input end 304 and the second outlet end 306, respectively, allow the housing 302 to be coupled with flanged pipes for easy installation into a typical oil pumping installation. The housing 302 can be made of steel, copper, iron, PVC (which can be opaque, translucent, or clear for viewing the flow of fluid), or another suitable material as desired for a particular application.

An orifice plate 312 can be disposed within the housing 302 to restrict the flow of fluid passed through an interior passage 314 of the housing 302. The orifice plate 312 can be used to contain the flow of fluid to cover sensors arrayed with the interior passage 314 of the housing 302. Also, the orifice plate 312 can be used to establish a controlled impediment in the flow of fluid for purposes of obtaining dynamic properties of the fluid, as will be described below.

Among the sensors arrayed in the interior passage 314 of the housing 302, in one exemplary embodiment, is a capacitance sensor 316. The capacitance sensor 316 suitably is a pair of insulated electrodes disposed to measure capacitance of the flow of fluid through the housing 302. The capacitance sensor 316 is coupled with conductors (not shown) used to measure capacitance of the flow of fluid passing through the interior passage 314. As previously described in connection with FIG. 2, a flow of fluid including oil yields an oscillating signal in proportion to the capacitance of the flow of fluid. As a result, the capacitance of the flow of fluid can be measured by creating an RC oscillator circuit through the capacitance sensor 306.

Also deployed in the interior passage 314 is a conductance sensor 318. In one presently preferred embodiment, the conductance sensor 308 also is an insulated device. A conductance sensor 308 may employ non-insulated electrodes. However, because of salinity of the water expected in the flow of fluid which can corrode non-insulated electrodes, an insulated device is preferable. The conductance sensor 308 suitably may be an AC capacitance sensor which, through application of an alternating signal, measures conductance of a flow of fluid adjacent to the conductance sensor. An output signal of the conductance sensor 308 (not shown) allows for the conductance to be measured for determining the proportional composition of the flow of fluid.

It will be appreciated that the capacitance sensor 316 and the conductance sensor 318 could be a single device. Adding appropriate supporting circuitry, appropriate signals can measure capacitance and conductance through electrodes of a single device. In such a configuration, the unified sensor would alternate between being a capacitance sensor 316 and a conductance sensor 318 depending on a mode directed by the supporting circuitry.

One embodiment of the device 300 involves only the capacitance sensor 316 and the conductance sensor 318 disposed within the interior passage 314 of the housing 302. Conductors coupled with the capacitance sensor 316 and the conductance sensor 318 allow for the capacitance and conductance of the flow of fluid through the interior passage 314 to be measured to determine a relative amount of oil in the fluid.

If desired in other embodiments of the present invention, additional sensors allow for measurements to be made of the total amount of fluid passing through the interior passage 314 and to adjust such measurements for pressure, density, temperature, or other factors. For example, a flow sensor 320 disposed in the interior passage 314 of the housing 302 suitably is a calorimetric flow sensor or other, similar device operable to monitor a rate of the flow of fluid. An output (not shown) of the flow sensor 320 indicating the rate of the flow of fluid can be combined with relative proportion measurements yielded by the capacitance sensor 316 and the conductance sensor 318 to determine a total flow rate of oil in the flow of fluid. In other words, the capacitance and conductance of the flow fluid can determine what proportion of the flow of fluid is oil, and multiplying that proportion by the total rate of flow yields the total rate of flow of oil being drawn through the measuring device 300.

The total rate of flow of oil can be affected by pressure, density, and temperature of the flow of fluid. Accordingly, if a measurement adjusted for these variables is desired, the measuring device 300 can include sensors to measure these properties and the resulting measurement can be used to adjust the measurements previously calculated. A pressure sensor 312 can be deployed on the support structure 304 to gauge the pressure of the flow. The pressure sensor 312 suitably is one of a number of types. A microelectronic machined silicon (MEMS) sensor having an integrated circuit including a sensing element and measuring electronics can be used. Alternatively, a piezoresistive sensor, or any other suitable pressure-sensing device may be used. A temperature sensor 314 can be disposed on the support structure 304 to measure the temperature of the flow of fluid. The temperature sensor 314 suitably is a thermocouple or other similar temperature-sensing device. A density probe 316 also can be deployed on the support structure 304 to measure the density of the flow of fluid. The density probe 316 may be a nuclear density probe or another suitable device. Each of these sensors is coupled with suitable signal lines that can be coupled to a computing device to collect their measurements such that they can be applied to adjust the measurements previously collected.

Figure 4:
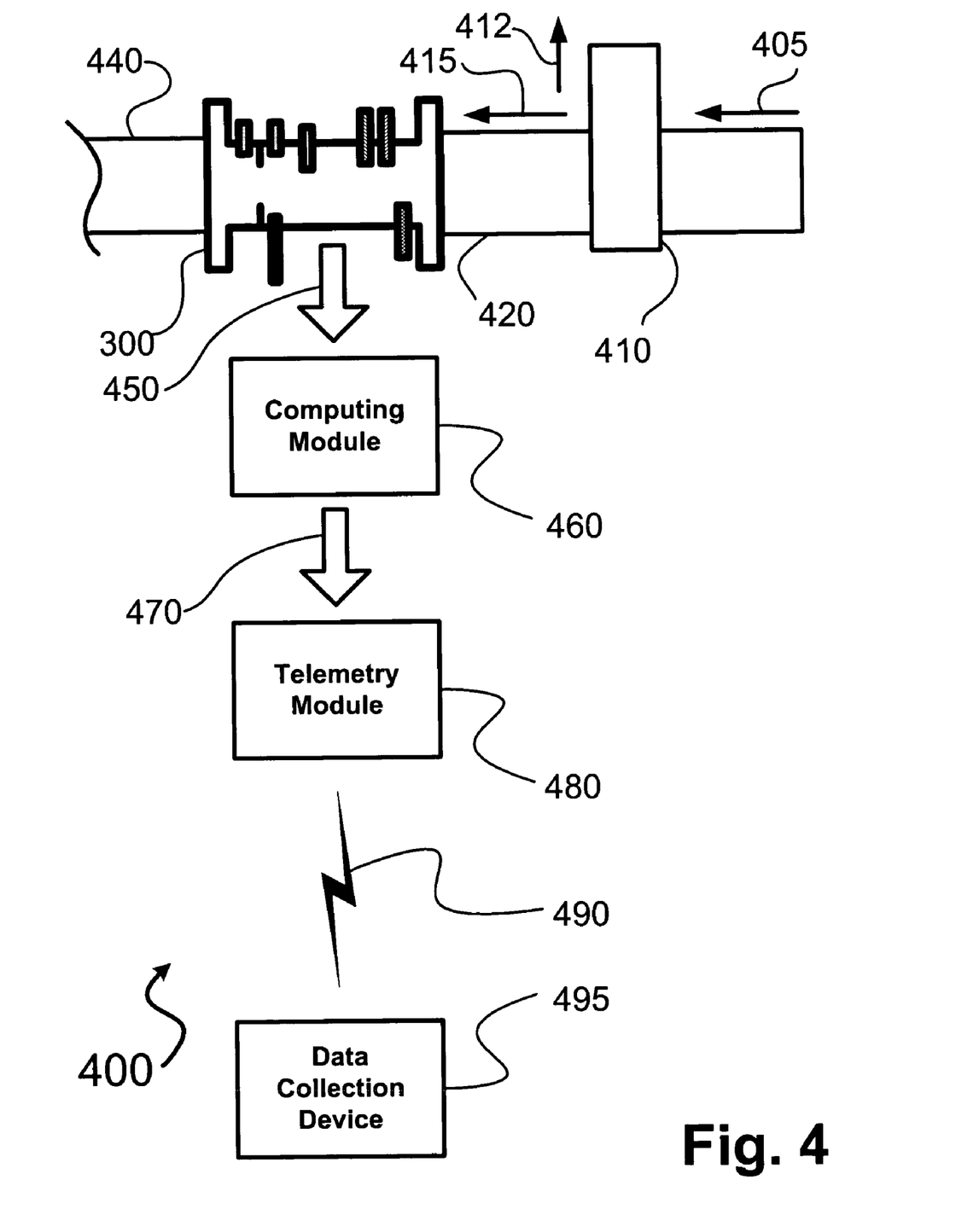
FIG. 4 is a block diagram of the measuring device of FIG. 3 and a system for collecting data yielded by the measuring device.

FIG. 4 is a block diagram of the measuring device 300 (FIG. 3) and a system 400 for collecting data yielded by the measuring device 300 in one presently preferred embodiment. The measuring device 300 is coupled with a source of the flow of fluid 415 via a pipeline or other vessel 420. A gas separation device 410, which suitably is a gas liquid cylindrical cyclone separator or a comparable device, separates liquid from gas. The gas separation device 410 receives a composite flow 405 containing at least one of oil, water, and gas. The gas separation device 410 separates the gas from the liquid, resulting in a separated flow of gas 412 diverted from the flow of fluid 415. The flow of fluid 415 passes through the measuring device 300 to a pipeline 440 routing the flow of fluid to a destination (not shown).

The measuring device 300 is coupled via a communication device 450 to a computing module 450. The communication device 450 suitably includes a plurality of conductors directly joining the sensors directly to a computing module 460. In this exemplary embodiment, output of the sensors 316, 318, 320, 322, and 324 is represented by analog signals. Alternatively, an analog-to-digital converter (not shown) may be included within the measuring device 300 itself, with an output of the analog-to-digital converter being coupled to the computing module 460. The digitized output of the sensors deployed in the measuring device 300 may be coupled to an interface, such as an RS-232 interface, which is coupleable to a complementary connector on the computing module 460.

The computing module 460 digitizes and processes the analog signals or processes the digital signals from the sensors 316, 318, 320, 322, and 324 (FIG. 3) as previously described. The computing module 460 receives the capacitance and conductance signals from the capacitance sensor 316 and the conductance sensor 318, respectively. The computer module 460 uses the digital or digitized signals to determine the proportion of oil in the flow of fluid. The proportion of oil in the flow of fluid can be combined with output of the flow rate sensor 320 to calculate the total rate of flow of oil. The total rate of flow of oil can be adjusted for pressure, density, and temperature measurements taken of the flow of fluid as previously described.

An output of the computing module 460 is coupled through a suitable communications interface 470 to a telemetry module 480. The telemetry module 480 is used to communicate results of the measurements made by the measuring device 300 and/or calculations performed by the computing module 460 via a communications medium 490 to a data collection device 495 that advantageously can be remotely located from the flow of fluid being measured. At the data collection device 495, data can be reviewed to monitor the production or viability of the well without having to be present locally at the measuring device 300 to monitor the flow of fluid.

Many variations on the system 400 are possible. To name a few non-limiting examples, operators of the system might choose to directly monitor the capacitance and the conductance of the fluid and have that data relayed to the data collection device 495. Sensors may be chosen that generate digital data, obviating use of the analog-to-digital converting circuit. Alternatively, the operators may wish to measure only the proportion of oil in the flow of fluid and communicate those signals from the measuring device 300 to the data collection device 495. Those measurements suitably are performed in hardware built into the measuring device 300 or within the computing module 460.

Alternatively, the operators of the system 400 may want information regarding the total rate of flow of oil with or without the capacitance, conductance, or proportion of oil in the flow of fluid data relayed to the data collection device 495. Similarly, the operators may want the total rate of flow of oil adjusted for one or more of pressure, density, and temperature, with or without the other data. Computations and adjustments suitably are made at the measuring device 300, in the computing module 460, at the data collection device 495, or at other locations as desired. Many permutations of the type of data communicated and where the data is received and/or manipulated are possible using embodiments of the present invention.

Similarly, different types of data communication systems suitably are used. The telemetry module 480 and the data communications network 490 could be a wired or wireless telemetry system configured to communicate with a remote data collection device 495. The data communications network 490 could be a telephone system, the Internet, a private Intranet, or another data network. Alternatively, the telemetry module 480 and the data communications network 490 could simply be a coupling and a cable to a nearby or on-site data collection device. The data may be communicated in real time or in batch mode. Again, many permutations are possible using embodiments of the present invention.

Figure 5:
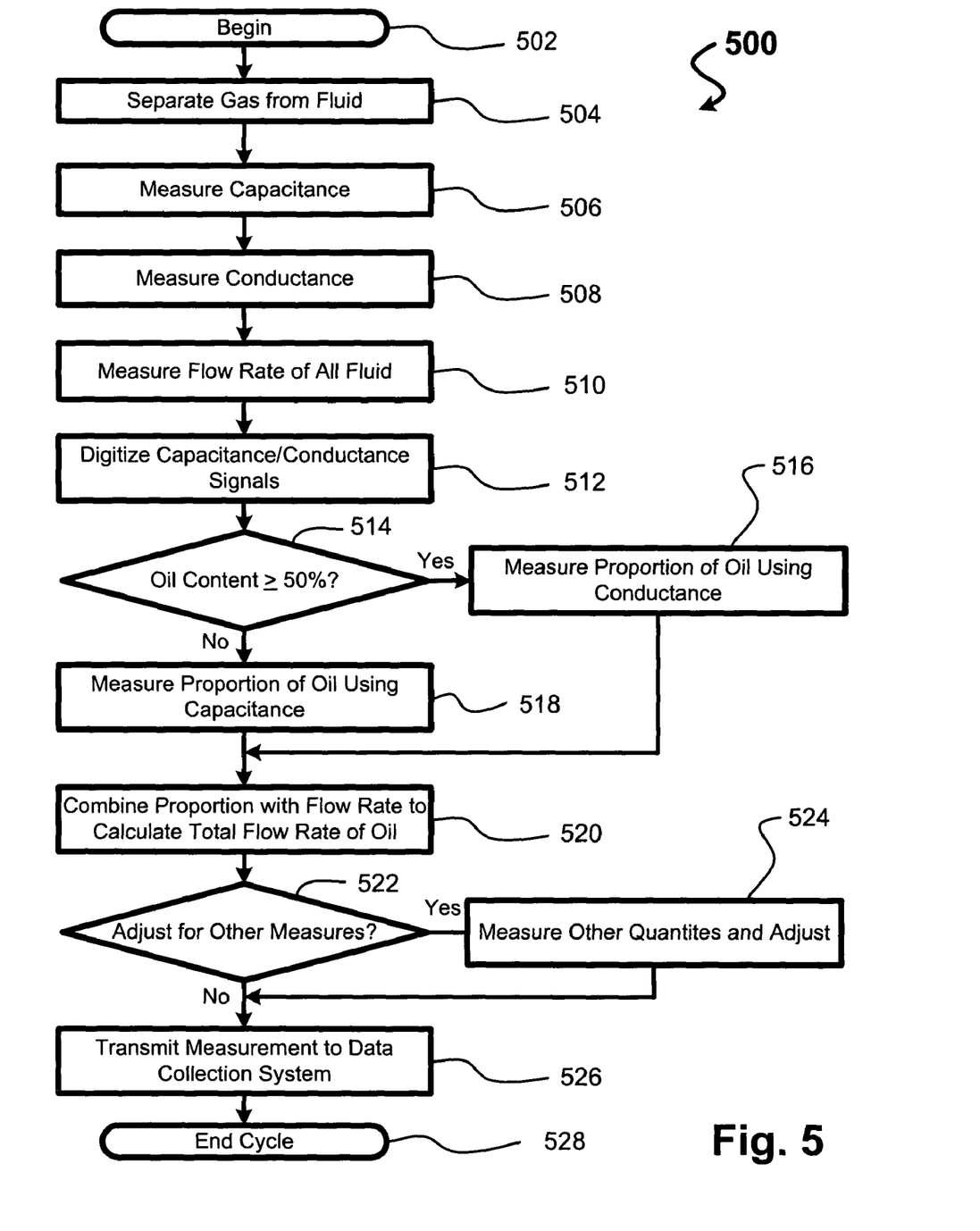
FIG. 5 is a flowchart of a routine using an embodiment of the present invention.

FIG. 5 is a flowchart of one presently preferred routine 500 using an embodiment of the present invention. The routine 500 begins at a block 502. At a block 504, gas is separated from the flow of fluid as previously described. At a block 506, the capacitance of the flow of fluid is measured. At a block 508, the conductance of the flow of fluid is measured. These measurements can take place simultaneously or in an order as desired.

In one presently preferred embodiment, at a block 510 a flow rate of the fluid is measured such that a proportion of the amount of oil in the flow of fluid can be multiplied by the flow rate to calculate the total rate of flow of oil. At a block 512, these measurements are digitized if such measurements are not already provided in digital form.

At a decision block 514, it is determined if the oil content is less than approximately one-half of the flow of fluid. This determination can be made by using one of or both the capacitance and conductance measurements to roughly gauge the proportion of oil in the flow of fluid. If the flow of fluid includes less than approximately one-half oil, at a block 516 the proportion of oil is calculated based on the conductance measured. On the other hand, if it is determined at the decision block 514 that the flow of fluid is not less than approximately one-half oil, at a block 518 the proportion of oil is calculated based on the capacitance measured. Depending on the approximate determination of the proportion of oil made at the decision block 514, it may be desirable to use both conductance and capacitance and weigh the calculations yielded from both.

At a block 520, the proportion of oil found in the flow of fluid is combined with the flow rate of the fluid to determine the total rate of flow of oil. At a decision block 522 it is determined whether it is desired to adjust the calculation of the total rate of flow of oil for other measurements such as pressure, density, and temperature. Such a determination can be predetermined or made based on measurements of pressure, density, or temperature that transcend predetermined thresholds. If it is desired to adjust the total rate of flow of oil for these other measures, at a block 524 these other measurements are made and/or applied to adjust the total rate of flow of oil. Once the adjustments are made or if no adjustments are desired, at a block 526 the resulting data is transmitted to a data collection device. The routine 500 ends at a block 528. The routine 500 could be repeated continually, at intervals, on demand, or as otherwise desired.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. An apparatus for measuring an amount of oil in a flow of fluid, the apparatus comprising:
   a housing defining an interior passage configured to pass a flow of fluid therethrough;
   a capacitance sensor configured to respond to a capacitance of the flow of fluid, the capacitance sensor being disposed within the interior passage of the housing and coupled to conductors; and
   a conductance sensor configured to measure conductance of the flow of fluid, the conductance sensor being disposed on the interior passage of the housing and being further configured to generate a conductance signal.

2. The apparatus of claim 1, further comprising a control module operably coupled to the conductors and the conductance signal, the control module being further configured to measure a capacitance of the flow of fluid and generate a first signal representative of the capacitance of the flow of fluid and convey a second signal representative of the conductance of the flow of fluid.

3. The apparatus of claim 1, wherein the housing includes a first end coupled with an outlet of a source of the flow of fluid and a second end.

4. The apparatus of claim 3, wherein the first and second ends of the housing include flanges such that the flanges are coupleable with flanged pipe sections.

5. The apparatus of claim 1, wherein the housing includes one of a steel pipe, an iron pipe, a copper pipe, an opaque PVC pipe, a translucent PVC pipe, or a clear PVC pipe.

6. The apparatus of claim 1, further comprising an orifice plate disposed within the interior passage of the housing, the orifice plate being configured to restrict the flow of fluid through the interior passage such that the flow of fluid is directed over the capacitance sensor and the conductance sensor.

7. The apparatus of claim 1, wherein the capacitance sensor is disposed on opposing sides of the interior passage of the housing.

8. The apparatus of claim 2, further comprising an analog-to-digital converting circuit configured to convert the first signal into a first digital signal and to convert the second signal into a second digital signal.

9. The apparatus of claim 8, wherein the control module includes an interface configured to communicate the first and second digital signals.

10. The apparatus of claim 9, wherein the interface includes an RS-232 interface.

11. The apparatus of claim 9, further comprising a first telemetry module configured to receive the first and second digital signals from the interface and to communicate the first and second digital signals to a data collection device.

12. The apparatus of claim 9, further comprising a computing module configured to receive the first and second digital signals from the interface and compute a relative amount of oil in the flow of fluid, the computing module being further configured to generate a relative amount of oil signal.

13. The apparatus of claim 12, wherein the computing module is configured to use the first digital signal to calculate the relative amount of oil in the flow of fluid when at least one of the first and second digital signals indicates that approximately not less than one-half of the flow of fluid includes oil, and to use the second digital signal to calculate the relative amount of oil in the flow of fluid when at least one of the first and second digital signals indicate that approximately not more than one-half of the flow of fluid includes oil.

14. The apparatus of claim 12, further comprising a second telemetry module configured to communicate the relative amount of oil signal to the data collection device.

15. The apparatus of claim 13, further comprising a flow rate sensor disposed on the interior passage of the housing, the flow rate sensor being configured to measure a total rate of the flow of fluid passing through the interior passage of the housing and to generate a flow rate signal.

16. The apparatus of claim 15, wherein the computing module is further configured to combine the relative amount of oil in the flow of fluid with the flow rate signal for calculating a total flow rate of oil in the flow of fluid, the computing module being further configured to generate a total flow rate of oil signal.

17. The apparatus of claim 16, further comprising a third telemetry module configured to communicate the total flow rate of oil signal to the data collection device.

18. The apparatus of claim 16, further comprising at least one additional fluid property sensor disposed on the interior passage of the housing, the at least one additional fluid property sensor being configured to measure an additional fluid property of the flow of fluid passing through interior passage of the housing and generate a fluid property signal.

19. The apparatus of claim 18, wherein the computing module is further configured to combine the fluid property signal with the total flow rate of oil in the flow of fluid for calculating an adjusted total flow rate of oil in the flow of fluid, the computing module being further configured to generate an adjusted total flow rate of oil signal.

20. The apparatus of claim 18, further comprising a fourth telemetry module configured to communicate the adjusted amount of oil signal to the data collection device.

21. The apparatus of claim 18, wherein the at least one additional fluid property sensor includes at least one pressure sensor configured to measure a pressure of the flow of fluid passing through the interior passage of the housing and the fluid property signal includes a fluid pressure signal.

22. The apparatus of claim 18, wherein the at least one additional fluid property sensor includes a density sensor configured to measure a density of the flow of fluid passing through the interior passage of the housing and the fluid property signal includes a fluid density signal.

23. The apparatus of claim 22, wherein the density sensor includes a nuclear density sensor.

24. The apparatus of claim 18, wherein the at least one additional fluid property sensor includes a temperature sensor configured to measure a temperature of the flow of fluid passing through the interior passage of the housing and the fluid property signal includes a temperature signal.

25. The apparatus of claim 3, further comprising a gas separator coupled between the first end of the housing and the source of the flow of fluid, the gas separator being configured to allow separation of gas from the flow of fluid.

26. A system for measuring an amount of oil in a flow of fluid, the apparatus comprising:
   a housing defining an interior passage configured to pass a flow of fluid therethrough;
   a capacitance sensor configured to respond to a capacitance of the flow of fluid, the capacitance sensor being disposed within the interior passage of the housing and coupled to conductors;
   a control module operably coupled to the conductors, the control module being configured to measure a capacitance of the flow of fluid and generate a first analog signal representing the capacitance of the flow of fluid;
   a conductance sensor configured to measure conductance of the flow of fluid disposed on the interior passage of the housing and generate a second analog signal representing the conductance of the flow of fluid;
   an analog-to-digital converter receiving the first and second analog signals and configured to convert the first analog signal into a first digital signal and to convert the second analog signal into a second digital signal;
   a computing module configured to receive the first and second digital signals and compute a relative amount of oil in the flow of fluid, the computing module being further configured to generate a relative amount of oil signal; and
   an interface configured to receive the relative amount of oil signal and communicate the relative amount of oil signal.

27. The system of claim 26, wherein the housing includes a first end coupled with an outlet of a source of the flow of fluid and a second end.

28. The apparatus of claim 27, wherein the first and second ends of the housing include flanges such that the flanges are coupleable with flanged pipe sections.

29. The apparatus of claim 26, wherein the housing includes one of a steel pipe, an iron pipe, a copper pipe, an opaque PVC pipe, a translucent PVC pipe, or a clear PVC pipe.

30. The apparatus of claim 26, further comprising an orifice plate disposed within the interior passage of the housing, the orifice plate being configured to restrict the flow of fluid through the interior passage such that the flow of fluid is directed over the capacitance sensor and the conductance sensor.

31. The apparatus of claim 26, wherein the capacitance sensor is disposed on opposing sides of the interior passage of the housing.

32. The apparatus of claim 26, wherein the interface includes an RS-232 interface.

33. The apparatus of claim 26, further comprising a first signal telemetry module configured to receive the relative amount of oil signal from the interface and to communicate the relative amount of oil signal to a data collection device.

34. The apparatus of claim 26, wherein the computing module is configured to use the first digital signal to calculate the relative amount of oil in the flow of fluid when at least one of the first and second digital signals indicates that approximately not less than one-half of the flow of fluid includes oil, and to use the second digital signal to calculate the relative amount of oil in the flow of fluid when at least one of the first and second digital signals indicate that approximately not more than one-half of the flow of fluid includes oil.

35. The apparatus of claim 34, further comprising a flow rate sensor disposed on the interior passage of the housing, the flow rate sensor being configured to measure a total rate of the flow of fluid passing through the interior passage of the housing and to generate a flow rate signal.

36. The apparatus of claim 35, wherein the computing module is further configured to combine the relative amount of oil in the flow of fluid with the flow rate signal for calculating a total flow rate of oil in the flow of fluid, the computing module being further configured to generate a total flow rate of oil signal.

37. The apparatus of claim 36, further comprising a second telemetry module configured to communicate the total flow rate of oil signal to the data collection device.

38. The apparatus of claim 36, further comprising at least one additional fluid property sensor disposed on the interior passage of the housing, the at least one additional fluid property sensor being configured to measure an additional fluid property of the flow of fluid passing through interior passage of the housing and generate a fluid property signal.

39. The apparatus of claim 38, wherein the computing module is further configured to combine the fluid property signal with the total flow rate of oil in the flow of fluid for calculating an adjusted total flow rate of oil in the flow of fluid, the computing module being further configured to generate an adjusted amount of oil signal.

40. The apparatus of claim 39, further comprising a third telemetry module configured to communicate the adjusted amount of oil in the flow of fluid to the data collection device.

41. The apparatus of claim 38, wherein the at least one additional fluid property sensor includes at least one pressure sensor configured to measure a pressure of the flow of fluid passing through the interior passage of the housing and the fluid property signal includes a fluid pressure signal.

42. The apparatus of claim 38, wherein the at least one additional fluid property sensor includes a density sensor configured to measure a density of the flow of fluid passing through the interior passage of the housing and the fluid property signal includes a fluid density signal.

43. The apparatus of claim 42, wherein the density sensor includes a nuclear density sensor.

44. The apparatus of claim 38, wherein the at least one additional fluid property sensor includes a temperature sensor configured to measure a temperature of the flow of fluid passing through the interior passage of the housing and the fluid property signal includes a temperature signal.

45. The apparatus of claim 27, further comprising a gas separator coupled between the first end of the housing and the source of the flow of fluid, the gas separator being configured to allow separation of gas from the flow of fluid.

46. A system for measuring an amount of oil in a flow of fluid, the apparatus comprising:
   a housing defining an interior passage configured to pass a flow of fluid therethrough;
   a capacitance sensor configured to respond to a capacitance of the flow of fluid, the capacitance sensor being disposed within the interior passage of the housing and coupled to conductors;
   a control module operably coupled to the conductors, the control module being configured to measure a capacitance of the flow of fluid and generate a first analog signal representing the capacitance of the flow of fluid;
   a conductance sensor configured to measure conductance of the flow of fluid disposed on the interior passage of the housing and generate a second analog signal representing the conductance of the flow of fluid;
   a flow rate sensor disposed on the interior passage of the housing, the flow rate sensor being configured to measure a total rate of the flow of fluid passing through interior passage of the housing and generate a third analog signal representing the total flow rate signal;
   an analog-to-digital converting receiving the first, second, and third analog signals and configured to convert the first analog signal into a first digital signal, to convert the second analog signal into a second digital signal, and to convert the third analog signal into a third digital signal;
   a computing module configured to receive the first, second, and third digital signals and compute a total flow rate of oil in the flow of fluid, the computing module being further configured to generate a total flow rate of oil signal; and
   an interface configured to receive the total flow rate of oil signal and communicate the total flow rate of oil signal.

47. The system of claim 46, wherein the housing includes a first end coupled with an outlet of a source of the flow of fluid and a second end.

48. The apparatus of claim 47, wherein the first and second ends of the housing include flanges such that the flanges are coupleable with flanged pipe sections.

49. The apparatus of claim 46, wherein the housing includes one of a steel pipe, an iron pipe, a copper pipe, an opaque PVC pipe, a translucent PVC pipe, or a clear PVC pipe.

50. The apparatus of claim 46, further comprising an orifice plate disposed within the interior passage of the housing, the orifice plate being configured to restrict the flow of fluid through the interior passage such that the flow of fluid is directed over the capacitance sensor and the conductance sensor.

51. The apparatus of claim 46, wherein the capacitance sensor is disposed on opposing sides of the interior passage of the housing.

52. The apparatus of claim 46, wherein the interface includes an RS-232 interface.

53. The apparatus of claim 46, further comprising a first signal telemetry module configured to receive the total flow rate of oil signal and to communicate the total flow rate of oil signal to a data collection device.

54. The apparatus of claim 46, wherein the computing module is configured to use the first digital signal to calculate the relative amount of oil in the flow of fluid when at least one of the first and second digital signals indicates that approximately not less than one-half of the flow of fluid includes oil, and to use the second digital signal to calculate the relative amount of oil in the flow of fluid when at least one of the first and second digital signals indicate that approximately not more than one-half of the flow of fluid includes oil.

55. The apparatus of claim 46, further comprising at least one additional fluid property sensor disposed on the interior passage of the housing, the at least one additional fluid property sensor being configured to measure an additional fluid property of the flow of fluid passing through interior passage of the housing and generate a fluid property signal.

56. The apparatus of claim 55, wherein the computing module is further configured to combine the fluid property signal with the total flow rate of oil in the flow of fluid for calculating an adjusted total flow rate of oil in the flow of fluid.

57. The apparatus of claim 56, further comprising a second telemetry module configured to communicate the total flow rate of oil in the flow of fluid to the data collection device.

58. The apparatus of claim 55, wherein the at least one additional fluid property sensor includes at least one pressure sensor configured to measure a pressure of the flow of fluid passing through the interior passage of the housing and the fluid property signal includes a fluid pressure signal.

59. The apparatus of claim 55, wherein the at least one additional fluid property sensor includes a density sensor configured to measure a density of the flow of fluid passing through the interior passage of the housing and the fluid property signal includes a fluid density signal.

60. The apparatus of claim 59, wherein the density sensor includes a nuclear density sensor.

61. The apparatus of claim 55 wherein the at least one additional fluid property sensor includes a temperature sensor configured to measure a temperature of the flow of fluid passing through the interior passage of the housing and the fluid property signal includes a temperature signal.

62. The apparatus of claim 47, further comprising a gas separator coupled between the first end of the housing and the source of the flow of fluid, the gas separator being configured to allow separation of gas from the flow of fluid.

63. A method for measuring an amount of oil in a flow of fluid, the apparatus comprising:

passing a flow of fluid from a source of fluid through a housing;

measuring a capacitance of the flow of fluid as the flow of fluid passes through the housing;

measuring the conductance of the flow of fluid as the flow of fluid passes through the housing;

calculating a relative amount of oil in the flow of fluid based on the capacitance of the flow of fluid when at least one of the capacitance and the conductance indicates that approximately not less than one-half of the flow of fluid includes oil and calculating the relative amount of oil in the flow of fluid based on the conductance when at least one of the capacitance and the conductance indicates that approximately not more than one-half of the flow of fluid includes oil; and generating a relative amount of oil signal.

64. The method of claim 63, further comprising communicating the relative amount of oil signal to a data collection device.

65. The method of claim 63, further comprising measuring a rate of flow of fluid through the housing.

66. The method of claim 65, further comprising calculating a total flow rate of oil in the flow of fluid by combining the rate of flow of fluid with the relative amount of oil in the flow of fluid and generating a total flow rate of oil signal.

67. The method of claim 66, further comprising communicating the total flow rate of oil signal to the data collection device.

68. The method of claim 66, further comprising measuring at least one additional fluid property of the flow of fluid passing through the housing.

69. The method of claim 68, further comprising calculating an adjusted total flow rate of oil in the flow of fluid by combining the total flow rate of oil in the flow of fluid with the additional property of the flow of fluid and generating an adjusted amount of oil signal.

70. The method of claim 69, further comprising communicating the adjusted total flow rate of oil signal to the data collection device.

71. The method of claim 68, wherein the at least one additional fluid property includes fluid pressure.

72. The method of claim 68, wherein the at least one additional fluid property includes fluid density.

73. The method of claim 68, wherein the at least one additional fluid property includes fluid temperature.

74. The method of claim 63, further comprising separating gas from the flow of fluid before directing the flow of fluid from the source of fluid through the housing.

75. A method for measuring an amount of oil in a flow of fluid, the apparatus comprising:

passing a flow of fluid from a source of fluid through a housing;

measuring a capacitance of the flow of fluid as the flow of fluid passes through the housing;

measuring the conductance of the flow of fluid as the flow of fluid passes through the housing;

measuring a rate of flow of fluid through the housing;

calculating a relative amount of oil in the flow of fluid based on the capacitance of the flow of fluid when at least one of the capacitance and the conductance indicates that approximately not less than one-half of the flow of fluid includes oil and calculating the relative amount of oil in the flow of fluid based on the conductance when at least one of the capacitance and the conductance indicates that approximately not more than one-half of the flow of fluid includes oil;

calculating a total flow rate of oil in the flow of fluid by combining the rate of flow of fluid with the relative amount of oil in the flow of fluid; and generating a total flow rate of oil signal.

76. The method of claim 75, further comprising communicating the total flow rate of oil signal to a data collection device.

77. The method of claim 75, further comprising measuring at least one additional fluid property of the flow of fluid passing through the housing.

78. The method of claim 77, further comprising calculating an adjusted total flow rate of oil in the flow of fluid by combining the total flow rate of oil in the flow of fluid with the additional property of the flow of fluid and generating an adjusted total flow rate of oil signal.

79. The method of claim 78, further comprising communicating the adjusted total flow rate of oil signal to the data collection device.

80. The method of claim 77, wherein the at least one additional fluid property includes fluid pressure.

81. The method of claim 77, wherein the at least one additional fluid property includes fluid density.

82. The method of claim 77, wherein the at least one additional fluid property includes fluid temperature.

83. The method of claim 77, further comprising communicating the adjusted total flow rate of oil in the flow of fluid to the data collection device.

84. The method of claim 75, further comprising separating gas from the flow of fluid before directing the flow of fluid from the source of fluid through the housing.

* * * * *